United States Patent [19]

Bugaut et al.

[11] 4,277,244

[45] Jul. 7, 1981

[54] DYE COMPOSITIONS FOR KERATINIC FIBERS CONTAINING PARAPHENYLENEDIAMINES

[75] Inventors: Andree Bugaut, Boulogne; Patrick Andrillon, Aulnay, both of France

[73] Assignee: Societe Anonyme dite: L'Oreal, Paris, France

[21] Appl. No.: 9,943

[22] Filed: Feb. 6, 1979

Related U.S. Application Data

[63] Continuation of Ser. No. 722,818, Sep. 13, 1976, abandoned.

[30] Foreign Application Priority Data

Aug. 20, 1976 [FR] France .................... 76 25386

[51] Int. Cl.³ .................... C07C 91/06; A61K 7/12
[52] U.S. Cl. .................... 8/410; 8/411; 8/412; 564/443
[58] Field of Search .................... 8/10.2, 11, 32, 410, 8/411, 412; 260/573

[56] References Cited

U.S. PATENT DOCUMENTS

| | | | |
|---|---|---|---|
| B 430,334 | 1/1976 | Halasz .................... | 8/10.2 |
| 2,684,893 | 7/1954 | Hughes et al. .................... | 260/573 |
| 3,819,708 | 6/1974 | Manning .................... | 260/573 |
| 3,884,627 | 5/1975 | Brody et al. .................... | 8/477 |

OTHER PUBLICATIONS

Corbett, J. F. in Venkataraman's "The Chemistry of Synthetic Dyes", vol. V, (Academic Press), 1971, pp. 479–482.

*Primary Examiner*—A. Lionel Clingman
*Attorney, Agent, or Firm*—Cushman, Darby & Cushman

[57] ABSTRACT

A dyeing composition for keratinic fibers, especially human hair, comprising an aqueous solution containing a dyeing amount of at least one dye compound having the formula:

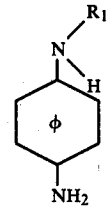

in which $R_1$ is —$(CH_2)_n$—$OR$, R is methyl or ethyl, n is 2 or 3, or one of the corresponding acid salts.

19 Claims, No Drawings

DYE COMPOSITIONS FOR KERATINIC FIBERS CONTAINING PARAPHENYLENEDIAMINES

This is a continuation of application Ser. No. 722,818 filed Sept. 13, 1976, abandoned.

It is known that the peraphenylenediamines play, in oxidation dyes for keratinic fibers and in particular hair, a very important well known role, whether they are used alone or in association with metaphenylenediamines, metaaminophenols, or metadiphenols. In order that an oxidation dye, and in particular a paraphenylenediamine, may be used as a hair dye, it must be innocuous, and it is also necessary that the shades imparted to the hair, during the application in an oxidizing alkaline medium, be stable in time, and in particular, resistant to light, to inclement weather, and to shampooing throughout the period which usually separates two successive hair dyeings.

The present invention relates to new paraphenylenediamines which are simultaneously innocuous for use as a hair dye and color stable.

The invention has, consequently, for its object the new industrial product which constitutes a chemical compound having the general formula:

in which formula $R_1$ represents a $(CH_2)_n$—OR radical, R being a methyl or ethyl radical, n being equal to 2 or 3 as well as the corresponding acid salts.

The present invention also has for its object the new industrial product which consists of a dyeing composition for keratinic fibers and in particular for human hair characterized by the fact that it contains in solution at least one compound of formula (I), or the corresponding acid salts.

In a preferred embodiment the composition according to the invention contains from 0.001% to 6% by weight of compounds of formula (I) in proportion to the total weight of the composition; in the case in which the composition contains compounds of formula (I) which are paraphenylenediamines having a secondary amine, particularly advantageous results are obtained by so operating that the concentration of the dyeing composition in paraphenylenediamines having a secondary amine according to the invention is between 0.001% and 6% by weight in proportion to the total weight of the composition.

The pH of the dyeing composition according to the invention is a basic pH for example between 8 and 11.5. A pH between 9 and 10 is preferred. Among the alkalizing agents which may be used one may mention ammonia, the alkylamines such as ethylamine or triethylamine, the alkanolamines such as the mono, the di, or the triethanolamines, the ammonium derivatives, the hydroxides of sodium or potassium, the carbonates of sodium or potassium.

The dyeing compositions according to the invention may contain one or several compounds of formula (I), they may also contain other paraphenylenediamines other than those defined by formula (I) such as, for example, the paraphenylenediamine, 5-methoxy paraphenylenediamine, 2,6-dimethyl-3-methoxy paraphenylenediamine, 2,6-dimethyl paraphenylenediamine, 4-amino-N,N-dihydroxyethyl aniline, 4-amino-N-ethyl-N-carbamylmethyl aniline. They may also contain paraaminophenols such as, for example, paraaminophenol, 2-methyl-4-amino phenol, 3-chloro-4-amino phenol.

The dyeing compositions according to the invention may also contain coupling agents, compounds which, in association with the paraphenylenediamines and the paraaminophenols lead, in an oxidizing alkaline medium, to colored indamines, indoanilines and indophenols. For example, they may contain:

(a) metaphenylenediamines such as 2,4-diamino anisole, 2,6-dimethyl metaphenylenediamine, 2,6-diamino pyridine, (2,4-diamino) phenoxyethanol, (2-amino-4-amino-N-methyl) phenoxyethanol, (2,4-diamino)-phenyl-β-methoxyethylether, (2,4-diamino)-phenyl mesylaminoethylether, 2-amino-4-amino-N-carbamylmethyl anisole;

(b) metaaminophenols such as metaaminophenol, 2-methyl-5-amino phenol, 2-methyl-5-amino-N-β-hydroxyethyl phenol;

(c) metadiphenols such as resorcin or orcin;

(d) metaacetylaminophenols such as 2,6-dimethyl-5-acetylamino phenol;

(e) 5-metacarbalkoxyamino phenols such as 2-methoxy-5-carbethoxyamino phenol;

(f) metaureidophenols such as 2-methyl-5-ureido phenol;

(g) 6-hydroxy phenomorpholine;

(h) 3-amino-4-methoxy phenol.

It must be noted that, for a given coupling agent, the results from the dyeing point of view differ according to whether the compound (I) possesses a secondary or tertiary amine function. For example, the metaaminophenols, 6-hydroxy phenomorpholine, resorcin, 2,6-dimethyl-5-amino phenol lead to colorations of much weaker chromaticity when the compound (I) has a tertiary amine function. With the metaphenylenediamines, the group of compounds (I) lead to colorations of good stability, strong chromaticity.

The compositions according to the invention may also contain direct dyes and in particular nitrated dyes of the benzene series such as, for example, 1-amino-N,N-dihydroxyethyl-3-nitro-4-amino-N'-methyl benzene, 1-amino-N,N-methyl-β-hydroxyethyl-3-nitro-4-amino-N'-β-hydroxyethyl benzene, 1-amino-N,N-methyl-β-hydroxyethyl-3-nitro-4-amino-N'-methyl benzene, 3-nitro-4-amino-N-β-hydroxyethyl anisole, 3-nitro-4-amino-N-β-hydroxyethyl phenol, (3-nitro-4-amino) phenoxyethanol, (3-nitro-4-amino-N-methyl) phenoxyethanol, 2-β-hydroxyethylamino-5-nitro anisole, 2-methyl-4-nitro aniline.

The compositions according to the invention may also contain leuco derivatives of indoanilines and indophenols such as 4,4'-dihydroxy-2-amino-5-methyl diphenylamine, 4,4'-dihydroxy-2-amino-N-β-hydroxyethyl-5-methyl-2'-chloro diphenylamine, 2,4'-diamino-4-hydroxy-5-methyl diphenylamine. They may also contain polyaminophenols, monoaminodiphenols, diaminodiphenols, and polyphenols such as trihydroxybenzene.

One may also add to the composition according to the invention hydrosoluble anionic, cationic, non-ionic or amphoteric surface-active agents. Among the surface-active agents particularly usable one may mention the alkylbenzene-sulfonates, the alkylnaphthalene-sulfonates, the sulfates, ether-sulfates and sulfonates of fatty alcohols, the quaternary ammonium salts such as triethylcetylammonium bromide, cetylpyridinium bromide, diethanolamides of fatty acids, the acids and polyoxyethylene alcohols and the polyoxyethylene alkylphenols. Preferably the surface-active agents are present in the compositions according to the invention in a proportion between 0.5 and 30% by weight and preferably between 4 and 25% in proportion to the total weight of the composition.

One may also add into the compositions according to the invention organic solvents for solubilizing the compounds which are not sufficiently soluble in water. Among the solvents which one may advantageously use, one may mention by way of example ethanol, isopropanol, glycerine, glycols such as butylglycol, ethylene-glycol, propylene-glycol, monoethylether and monomethylether of diethylene-glycol and analogous products.

The solvents may advantageously be present in the composition in a proportion going from 1 to 40% by weight and preferably from 5 to 30% by weight in proportion to the total weight of the composition.

The thickening products which one may add into the compositions according to the invention may advantageously be taken from the group formed by sodium alignate, gum arabic, cellulose derivatives such as methylcellulose, hydroxyethylcellulose, hydroxypropylmethylcellulose, the sodium salt of the carboxymethylcellulose and the polymers of acrylic acid; one may also use mineral thickening agents such as bentonite. Preferably the thickening agents are present in a proportion between 0.5 and 5% by weight and preferably between 0.5 and 3% by weight as compared with the total weight of the composition.

One may also add to the compositions according to the invention, anti-oxidizing agents; these agents may advantageously be taken from the group formed by sodium sulfite, thioglycolic acid, sodium acid sulfite, ascorbic acid, and hydroquinone. These anti-oxidizing agents may advantageously be present in the composition in a proportion between 0.05 and 1% by weight in proportion to the total of the composition.

The compositions according to the invention may also contain various additives habitually used in the cosmetic field such, for example, penetrating agents, sequestrating agents, and perfume.

As indicated, one of the essential values of the use of the compounds of formula (I) in hair dyes results from the particular shades which said compounds produce.

The compounds of formula (I) are particularly valuable for somber colors: browns, sometimes lightly shaded with violet for concentrations of the order of 3 to 6% by weight, gray-beige for concentrations of the order of 1 to 2% by weight. These colorations conferred on the keratinic fibers in an alkaline oxidizing medium by the compounds of formula (I) used alone are stable in time and permit one to obtain what the man skilled in the art calls depth of coloration. The obtaining of this depth plays a particularly important role in the formulation of dyeing compositions for deep shades. Moreover, the compounds of formula (I), when they are associated in an oxidizing alkaline medium with metaphenylenediamine or metaaminophenols confer on the keratinic fibers shades of strong chromaticly stable in time to the light, to inclement weather, and to shampooing. When the couplers are metaphenylenediamines such as 2,4-diamino anisole, (2,4-diamino) phenoxyethanol, (2-amino-4-amino-N-methyl) phenoxyethanol, (2,4-diamino) phenyl-$\beta$-methoxyethylether, (2,4-diamino) phenyl mesylaminoethylether, 2-amino-N-carbamylmethyl-4-amino anisole the compounds of formula (I), and in particular 4-amino-N-methoxyethyl aniline give rise in situ in the keratinic fiber treated by the dyeing composition blue indamines which do not cycle easily into red azines rapidly destroyed by the light. It is thus possible to obtain a strong and stable blue which is particularly important for the formulation of dyeing compositions, not only in order to obtain blacks and grays, but also to obtain chestnuts and in particular burnt chestnuts. When the coupling agents used with the compounds of the formula (I) are metaaminophenols such as metaaminophenol, 2-methyl-5-amino phenol, 2-methyl-5-amino-N-$\beta$-hydroxyethyl phenol, 2,6-dimethyl-3-amino phenol, it gives birth to indoanilines which confer to the keratinic fibers violet shade which is more or less purple of good quality. When the coupling agent used is 6-hydroxy benzomorpholine, one obtains with the compounds of formula (I), a very stable green coloration.

It follows from this detailed study that the compounds of formula (I) are particularly valuable for the production of dyeing compositions for the hair. As has already been indicated, all the compounds according to the invention make it possible to obtain simultaneously in their application in dyeing the hair a good innocuousness and a good stability of the shade in time. It must be noted that this double advantage does not exist when there is introduced into the benzene ring of the compound (I) a supplemental substitution: alkyl, alkoxy or halogen. It is thus that 3-methyl-4-amino-N-$\beta$-methoxyethyl aniline does not offer good innocuousness and 3-methoxy-4-amino-N-$\beta$-methoxyethyl aniline and 3-chloro-4-amino-N-$\beta$-methoxyethyl aniline do not lead to shades of good stability.

Moreover, these two latter products confer on the hair only shades of low chromaticity and 3-chloro-4-amino-N-$\beta$-methoxyethyl aniline does not keep during storage.

The compounds of formula (I) and their salts are obtained by processes of preparation of the conventional type within the scope of the man skilled in the art.

In order that the object of the invention may be better understood there will now be described in a purely illustrative and non-limiting way, several examples of preparation of compounds of formula (I) and several examples of the use of these compounds in dyeing compositions for hair.

EXAMPLE 1: Preparation of sulfate of 4-$\beta$-methoxyethylamino aniline

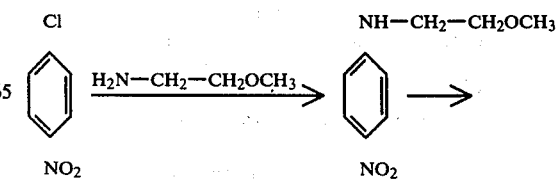

-continued

First step: Preparation of 4-nitro-N-β-methoxyethyl aniline

One heats to reflux for 15 hours 0.3 mole of parachloronitrobenzene (47.35 g) in solution in 150 ml of β-methoxyethylamine. One then pours the cooled reaction mixture into 300 g of crushed ice. The intended product precipitates first in the form of a red oil which crystallizes rapidly. After recrystallization in ethanol and drying under vacuum the product melts at 86° C. Analysis gives the following results:

| ANALYSIS | Calculated for $C_9H_{12}N_2O_3$ | FOUND |
|---|---|---|
| C % | 55.09 | 55.29 |
| H % | 6.17 | 6.39 |
| N % | 14.28 | 14.08 |

Second Step: Preparation of sulfate of 4-amino-N-β-methoxyethyl aniline.

To 115 ml of a hydroalcoholic solution (10% water, 90% alcohol) one adds 2 g of ammonium chloride and 30 g of zinc powder. This mixture is brought to reflux under agitation and then one adds little by little 0.1 mole (19.6 g) of 4-nitro-N-β-methoxyethyl aniline while regulating the addition in such a manner as to maintain the reflux without heating. When the addition of the nitrated derivative is terminated, the reaction mixture is colorless. It is filtered while recovering the filtrate in a phial containing 6.1 ml of iced sulfuric acid at 96%. The intended product precipitates in the form of sulfate. The sulfate is dryed, washed in acetone and recrystallized in a hydroalcoholic solution (70% alcohol, 30% water). After vacuum drying it melts while decomposing at 201° C.

Analysis gives the following results:

| ANALYSIS | calculated for $C_9H_{14}N_2O,SO_4H_2$ | FOUND |
|---|---|---|
| S % | 12.13 | 11.95–12.16 |

EXAMPLE 2: Preparation of dihydrochloride of 4-amino-γ-methoxypropyl aniline.

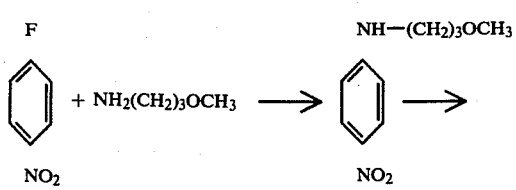

-continued

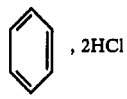

First step: Preparation of 4-nitro-N-γ-methoxypropyl aniline

One heats to reflux for 5 hours 0.2 mole (28.2 g) of parafluoronitrobenzene in 102 ml of γ-methoxypropylamine. One then pours the cooled reaction mixture into 200 g of crushed ice. The intended product precipitates first in the form of an oil which crystallizes rapidly. After recrystallization in methanol and vacuum drying the product melts at 56° C. Analysis gives the following results:

| ANALYSIS | Calculated for $C_{10}H_{14}N_2O_3$ | FOUND |
|---|---|---|
| C % | 57.13 | 57.25 |
| H % | 6.71 | 6.66 |
| N % | 13.33 | 13.57 |

Second Step: Preparation of dihydrochloride of 4-amino-N-γ-methoxypropyl aniline To 55 ml of hydroalcoholic solution (10% water, 90% alcohol) one adds 1 g of ammonium chloride and 25 g of zinc powder. One brings this mixture to reflux under agitation then one adds 0.05 mole (10.5 gr) of 4-nitro-N-γ-methoxypropylaniline while regulating the addition so as to maintain the reflux without heating. When the addition of the nitrated derivative is terminated, the reaction mixture is colorless. It is filtered while boiling in a phial containing 10.2 ml of hydrochloric acid at 36%. The expected product precipitates in the form of dihydrochloride. After drying under vacuum at 55° C., the product melts with decomposition at 190° C. Analysis gives the following results:

| ANALYSIS | Calculated for $C_{10}H_{16}N_2O,2HCl$ | FOUND |
|---|---|---|
| C % | 47.44 | 47.22 |
| H % | 7.17 | 7.31 |
| N % | 11.06 | 11.00 |
| Cl % | 28.01 | 27.91 |

EXAMPLE 3: Preparation of dihydrochloride of 4-amino-N-β-ethoxyethyl aniline

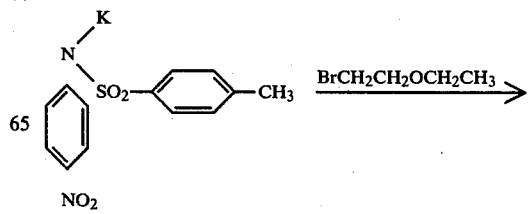

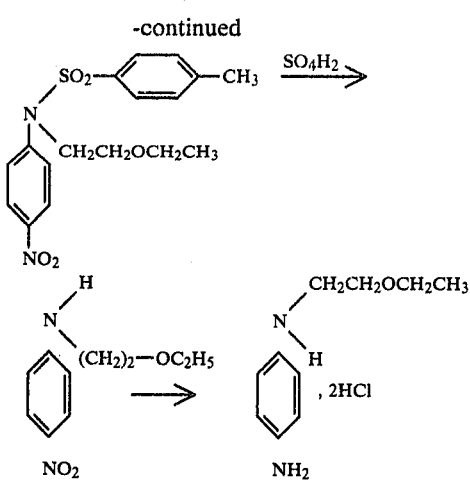

First step: Preparation of 1-amino-N-paratoluenesulfonyl-N-β-ethoxy-ethyl-4-nitro benzene One introduces 0.05 mole (16.5 g) of potassium salt of 1-amino-N-paratoluylenesulfonyl-4-nitro benzene into 40 ml of dimethylformamide. One heats the mixture in a boiling water bath then one introduces 0.06 mole (9.2 g) of technical 2-bromo ethoxyethane. One maintains the heating for 9 hours in the boiling water bath under agitation. One then pours the cooled reaction mixture into 200 g of crushed ice. The expected product precipitates in crystallized form. It is drained, washed with water and recrystallized in alcohol. After vacuum drying the product melts at 70° C.

Second step: Preparation of 1-amino-N-β-ethoxyethyl-4-nitro benzene

In 40 ml of sulfuric acid at 96% cooled to 0° C. one adds little by little under agitation 0.035 mole (12.75 g) of 1-amino-N-paratoluenesulfonyl-N-β-ethoxyethyl-4-nitro benzene. When the dissolution is complete, one abandons the reaction mixture for 3 hours at the ambient temperature then one pours it into 300 g of crushed ice. The expected product precipitates in the form of an oil which crystallizes rapidly. The product is left standing to dry, washed in water, dried and recrystallized in a mixture (benzene-hexane). After drying it melts at 46° C. The analysis gives the following results:

| ANALYSIS | Calculated for $C_{10}H_{14}N_2O_3$ | FOUND |
| --- | --- | --- |
| C % | 57.13 | 57.06 |
| H % | 6.71 | 6.82 |
| N % | 13.33 | 13.15 |

Third step: Preparation of dihydrochloride of 4-amino-N-β-ethoxyethyl aniline To 10 ml of alcohol at 96°, one adds 1 ml of water, 0.2 g of ammonium chloride, and 5 g of zinc powder. This mixture is brought to reflux and 0.02 mole (2.1 g) of 1-amino-N-β-ethoxyethyl-4-nitro benzene is added little by little under agitator. The addition completed, one maintains the reflux for several minutes until the reaction mixture loses its color completely. The reaction mixture is then filtered while boiling in a phial containing 2.05 ml of hydrochloric acid at 36%. By cooling the expected product precipitates in the form of dihydrochloride. After recrystallization in ethanol and vacuum drying the product melts with decomposition at 155° C. The calculated molecular weight for ($C_{10}H_{16}N_2O$, 2HCl) is 253. The molecular weight found by potentiometric analysis with the aid of an 0.1 soda solution is 256.

EXAMPLE 4

The following dyeing composition is prepared:

| | |
| --- | --- |
| 4-amino-N-methoxyethyl aniline sulfate (0.00015 mole) | 0.04g |
| Dihydrochloride of (2,4 diamino)-phenoxyethanol (0.00015 mole) | 0.036g |
| Propyleneglycol | 6.6 g |
| Oleic alcohol oxyethylenated with two moles of ethylene oxide | 3.3 g |
| Oleic alcohol oxyethylenated with 4 moles of ethylene oxide | 4.95 g |
| Ammonia at 22° Baume | 12 g |
| Water q.s. | 100 g |

The pH is 10.5. At the moment of use one adds 100 g of hydrogen peroxide at 20 volumes.

This mixture applied for 20 minutes at 25° C. on bleached hair imparts thereto after rinsing and shampooing a very luminous clear blue color.

EXAMPLE 5

The following dyeing composition is prepared:

| | |
| --- | --- |
| 4-amino-N-methoxyethyl aniline sulfate (0.0025 mole) | 0.66g |
| 2-methyl-5-amino-N-β-hydroxyethyl phenol (0.0025 mole) | 0.407g |
| Sodium laurylsulfate with 19% of starting oxyethylenated alcohol | 20.0g |
| Products sold under the tradename "Trilon B" | 0.2g |
| Ammonia at 22° B. | 10g |
| Sodium bisulfite at 40% | 1 g |
| Water q.s. | 100 g |

The pH is 10.7. At the moment of use 100 g of hydrogen peroxide at 20 volumes is added.

This composition applied to bleached hair for 20 minutes at 28° C. imparts thereto after rinsing and shampooing an intense violet purple coloration.

EXAMPLE 6

The following dyeing composition is prepared:

| | |
| --- | --- |
| 4-amino-N-methoxyethyl aniline sulfate (0.00088 mole) | 0.232 g |
| 2-methyl-5-amino phenol (0.00088 mole) | 0.10 g |
| Oleic alcohol oxyethylenated with 2 moles of ethylene oxide | 3.3 g |
| Oleic alcohol oxyethylenated with 4 moles of ethylene oxide | 4.9 g |
| Propyleneglycol | 6.6 g |
| Ammonia at 22° B. | 10 g |

The pH is 10.3. At the moment of use 70 g of hydrogen peroxide at 20 volumes is added.

This mixture applied to bleached hair for 20 minutes at 25° C. imparts thereto, after rinsing and shampooing, an intense very luminous PARME coloration.

EXAMPLE 7

The following dyeing composition is prepared:

| | |
| --- | --- |
| 4-N-methoxyethylamino aniline sulfate | 0.4 g |

-continued

| | |
|---|---|
| 6-hydroxy benzomorpholine | 0.23 g |
| Ammonium alkyl sulfate in $C_{12}$–$C_{14}$ (70% of $C_{12}$, 30% of $C_{14}$) | 15 g |
| Lauric alcohol having 10.5 moles of ethylene oxide | 5 g |
| Ammonia at 22° B. | 10 g |
| Water q.s. | 100 g |

The pH is 10.1. At the moment of use, 85 cm³ of hydrogen peroxide at 20 volumes is added.

This mixture, applied for 20 minutes at 25° C. on bleached hair imparts thereto, after rinsing and shampooing, an intense golden green coloration.

EXAMPLE 8

The following hair dyeing preparation is prepared:

| | |
|---|---|
| 4-methoxyethylamino aniline sulfate | 0.00125 g |
| Dihydrochloride of (2,4-diamino) phenyl-β-methoxyethyl ether | 0.0012 g |
| Butylglycol | 7.5 g |
| Ammonia at 22° B. | 7 g |
| Products known under the commercial name of "Carbopol 534" (Polymer of the acrylic acid MoW. = 2 to 3 millions manufactured by the Goodrich Chemical Company) | 3.37 g |
| Water, q.s. | 100 g |

The pH is 8. At the moment of use one adds 20 g of hydrogen peroxide at 20 volumes.

This mixture applied for 20 minutes at 20° C. on bleached hair imparts thereto, after rinsing and shampooing, a clear silver blue coloration.

EXAMPLE 9

The following preparation is prepared:

| | |
|---|---|
| 4-methoxyethylamino aniline sulfate | 0.66 g |
| Dihydrochloride of 2,4-diamino anisole | 0.527 g |
| Sodium laurylsulfate with 19% of starting oxyethylenated alcohol | 20 g |
| Product sold under the commercial name "Trilon B" | 0.2 g |
| Ammonia at 22° B. | 10 g |
| Sodium bisulfite at 40% | 1 g |
| Water, q.s. | 100 g |

The pH is 10.8. At the moment of use, one adds 70 g of hydrogen peroxide at 20 volumes.

This mixture applied for 20 minutes at 20° C. to bleached hair imparts thereto, after rinsing and shampooing, an intense clear blue coloration.

EXAMPLE 10

The following dyeing composition is prepared:

| | |
|---|---|
| 4-amino-N-methoxyethyl aniline sulfate | 1.5 g |
| Butylglycol | 20 g |
| Oleic alcohol oxyethylenated at 2 moles of ethylene oxide | 2.59 g |
| Oleic alcohol oxyethylenated at 4 moles of ethylene oxide | 3.85 g |
| Propyleneglycol | 5.18 g |
| Ammonia at 22° B. | 10 g |
| Water, q.s. | 100 g |

At the moment of use, one adds 100 g of hydrogen peroxide at 20 volumes.

This mixture applied for 25 minutes at 25° C. to bleached hair imparts thereto, after rinsing and shampooing, a deep grey beige coloration.

EXAMPLE 11

The following dyeing composition is prepared:

| | |
|---|---|
| 4-methoxyethylamino aniline sulfate | 4 g |
| Butylglycol | 10 g |
| Ammonia at 22° B. | 10 g |
| Carboxymethylcellulose | 3.25 g |
| Water, q.s. | 100 g |

The pH is 9.3. At the moment of use one adds 100 g of hydrogen peroxide at 20 volumes.

This mixture applied for 25 minutes at 20° to bleached hair imparts thereto, after rinsing and shampooing, a very sombre brown coloration with violet glints.

EXAMPLE 12

The following dyeing composition is prepared:

| | |
|---|---|
| 4-amino-N-methoxyethyl aniline sulfate | 6 g |
| Propyleneglycol | 6.6 g |
| Oleic alcohol oxyethylenated at 2 moles of ethylene oxide 3.3 g | |
| Oleic alcohol oxyethylenated at 4 moles of ethylene oxide | 4.95 g |
| Ammonia at 22° B. | 12 g |
| Water, q.s. | 100 g |

The pH is 9.3. At the moment of use one adds 100 g of hydrogen peroxide at 20 volumes.

This mixture applied for 20 minutes at 25° C. on bleached hair imparts thereto, after rinsing and shampooing, a black brown coloration with violet glints.

EXAMPLE 13

The following dyeing composition is prepared:

| | |
|---|---|
| 4-amino-N-methoxyethyl aniline sulfate | 3.3 g |
| Dihydrochloride of (2,4-diamino) phenoxyethanol | 0.03 g |
| Propyleneglycol | 6.6 g |
| Oleic alcohol oxyethylenated at 2 moles of ethylene oxide | 3.3 g |
| Oleic alcohol oxyethylenated at 4 moles of ethylene oxide | 4.95 g |
| Ammonia at 22° B. | 12 g |
| Water, q.s. | 100 g |

The pH is 9.15. At the moment of use one adds 100 g of hydrogen peroxide. This mixture applied for 20 minutes at 25° C. to bleached hair imparts thereto, after rinsing and shampooing, a raven black coloration.

This example illustrates the value of N-methoxyethylamino aniline used in great excess in proportion to the metaphenylenediamine to obtain very deep shades.

EXAMPLE 14

The following dyeing composition is prepared:

| | |
|---|---|
| 4-methoxyethylamino aniline sulfate | 3.43 g |
| Trihydroxybenzene | 1.61 g |
| Butylglycol | 4.5 g |
| Lauric alcohol oxyethylenated at 1.5 moles of ethylene oxide | 4.5 g |
| Triethanolamine | 11 g |
| Sodium bisulfite | 0.5 g |

| | |
|---|---|
| Water, q.s. | 100 g |

The pH is 8.1. At the moment of use one adds 80 g of hydrogen peroxide at 20 volumes.

This mixture applied for 30 minutes at 25° C. to bleached hair imparts thereto, after rinsing and shampooing, an anthracite coloration.

EXAMPLE 15

The following dyeing composition is prepared:

| | |
|---|---|
| 4-methoxyethylamino aniline sulfate | 0.3 g |
| 2-methyl-5-amino-N-$\beta$-hydroxyethyl phenol | 0.05 g |
| Paraaminophenol | 0.03 g |
| 2,6-dimethyl-5-acetylamino phenol | 0.2 g |
| Sodium laurylsulfate with 19% oxyethylenated starting alcohol | 20 g |
| Product known under the commercial name of "Trilon B" | 0.2 g |
| Ammonia at 22° B. | 10 g |
| Sodium bisulfite at 40% | 1 g |
| Water, q.s. | 100 g |

The pH is 10.5. At the moment of use one adds 100 g of hydrogen peroxide at 20 volumes.

This mixture applied for 20 minutes at 20° C. to bleached hair imparts thereto, after rinsing and shampooing, a silver grey coloration.

EXAMPLE 16

The following dyeing composition is prepared:

| | |
|---|---|
| 4-methoxyethylamino aniline sulfate | 0.15 g |
| Dihydrochloride of (2,4-diamino)phenylmesylaminoethylether | 0.05 g |
| Metaaminophenol | 0.05 g |
| Dihydrochloride of 2,6-diamino hydroquinone | 0.1 g |
| 4-amino-N-methyl phenol sulfate | 0.05 g |
| 2,4'-diamino-4-hydroxy-5-methyl diphenylamine | 0.08 g |
| (3-nitro-4-amino) phenoxyethanol | 0.15 g |
| 2-amino-N-$\beta$-hydroxyethyl-5-nitro anisole | 0.04 g |
| (3-nitro-4-amino-N-methyl) phenoxyethanol | 0.02 g |
| Sodium laurylsulfate with 19% oxyethylenated starting alcohol | 20 g |
| Product known under the commercial name of "Trilon B" | 0.2 g |
| Ammonia at 22° B. | 10 g |
| Sodium bisulfite at 40% | 1 g |
| Water, q.s. | 100 g |

The pH is 10.5. At the moment of use one adds 100 g of hydrogen peroxide at 20 volumes.

This mixture applied for 20 minutes at 25° C. on bleached hair imparts thereto, after rinsing and shampooing, a very clear golden chestnut coloration.

EXAMPLE 17

The following dyeing composition is prepared:

| | |
|---|---|
| 4-methoxyethylamino aniline sulfate | 0.15 g |
| Dihydrochloride of (2,4-diamino) phenylmesylaminoethylether | 0.05 g |
| Metaaminophenol | 0.05 g |
| 2-methyl-5-amino-N-$\beta$-hydroxyethyl phenol | 0.02 g |
| (3-nitro-4-amino)phenoxyethanol | 0.15 g |
| dihydrochloride of 2,6-diamino hydroquinone | 0.1 g |
| 4-amino-N-methyl phenol sulfate | 0.057 g |
| 2-amino-N-$\beta$-hydroxyethyl-5-nitro anisole | 0.06 g |
| 2,4'-diamino-4-hydroxy-5-methyldiphenylamine | 0.08 g |
| Sodium laurylsulfate with 19% oxyethylenated starting alcohol | 20 g |
| Product sold under the commercial name "Trilon B" | 0.2 g |
| Ammonia at 22° B. | 10 g |
| Sodium bisulfite at 40% | 1 g |
| Water, q.s. | 100 g |

The pH is 10.5. At the moment of use, 100 g of hydrogen peroxide at 20 volumes is added.

This mixture applied 20 minutes at 25° C. on bleached hair imparts thereto, after rinsing and shampooing, a golden black coloration.

EXAMPLE 18

The following dyeing composition is prepared:

| | |
|---|---|
| 4-methoxyethylamino aniline sulfate | 0.36 g |
| Dihydrochloride of 2,6-dimethyl-3-methoxy paraphenylenediamine | 0.17 g |
| Dihydrochloride of (2,4-diamino) phenoxyethanol | 0.05 g |
| 2-methyl-5-amino phenol | 0.07 g |
| 6-hydroxy benzomorpholine | 0.07 g |
| 3-nitro -4-amino-N-$\beta$-hydroxyethyl phenol | 0.02 g |
| (3-nitro-4-amino) phenoxyethanol | 0.035 g |
| Monomethylic ester of diethyleneglycol | 9 g |
| Ammonia at 22° B. | 10 g |
| Water, q.s. | 100 g |

The pH is 10. At the moment of use, one adds 100 g of hydrogen peroxide at 20 volumes.

This mixture applied for 20 minutes to 95% naturally white hair imparts thereto, after rinsing and shampooing, a metallic grey coloration.

EXAMPLE 19

The following coloring composition is prepared:

| | |
|---|---|
| 4-methoxyethylamino aniline sulfate | 0.16 g |
| Dihydrochloride of (2,4-diamino) phenoxyethanol | 0.10 g |
| Paraaminophenol | 0.30 g |
| Mataaminophenol | 0.22 g |
| (3-nitro-4-amino) phenoxyethanol | 0.13 g |
| Sodium laurylsulfate with 19% oxyethylenated starting alcohol | 20 g |
| Product known under the commercial name of "Trilon B" | 0.2 g |
| Ammonia at 22° B. | 10 g |
| Sodium bisulfite at 40% | 1 g |
| Water, q.s. | 100 g |

The pH is 10.5. At the moment of use, one adds 100 g of hydrogen peroxide at 20 volumes.

This mixture applied for 25 minutes at 20° C. on bleached hair imparts thereto, after rinsing and shampooing, a clear chestnut copper red coloration.

EXAMPLE 20

The following dyeing composition is prepared:

| | |
|---|---|
| 4-methoxyethylamino aniline sulfate | 0.004 g |
| Dihydrochloride of (2,4-diamino) phenyl-$\beta$-methoxyethylether | 0.0008 g |
| 2-methyl 5-amino-N-$\beta$-hydroxyethyl phenol | 0.0008 g |
| Ammonium alkyl sulfate in $C_{12}$–$C_{14}$ (70% $C_{12}$, 30% $C_{14}$) | 15 g |
| Lauric alcohol at 10.5 moles of ethylene oxide | 5 g |
| Ammonia at 22° B. | 10 g |
| Water, q.s. | 100 g |

The pH is 10.3. At the moment of use, one adds 10 g of hydrogen peroxide at 20 volumes.

This mixture applied for 30 minutes at 25° C. to bleached hair imparts thereto, after rinsing and shampooing, a clear slightly bluish silver grey.

EXAMPLE 21

The following dyeing composition is prepared:

| | |
|---|---|
| Dihydrochloride of 4-γ-methoxypropylamino aniline | 3 g |
| Butylglycol | 5 g |
| Lauric alcohol oxyethylenated at 10.5 moles of ethylene oxide | 5 g |
| Ammonia at 22° B. | 10 g |
| Water, q.s. | 100 g |

The final pH is 9.7. At the moment of use, one adds 100 ml of hydrogen peroxide at 20 volumes.

This mixture applied for 20 minutes at 25° C. on bleached hair imparts thereto, after rinsing and shampooing, a deep chestnut coloration.

EXAMPLE 22

The following dyeing composition is prepared:

| | |
|---|---|
| Dihydrochloride of 4-β-ethoxyethylamino aniline | 3 g |
| Butylglycol | 5 g |
| Lauric alcohol oxyethylenated at 10.5 moles of ethylene oxide | 5 g |
| Ammonia at 22° B. | 10 g |
| Water, q.s. | 100 g |

The final pH is 9.6. At the moment of use, one adds 100 g of hydrogen peroxide at 20 volumes.

This mixture applied to bleached hair for 20 minutes at 20° C. imparts thereto, after rinsing and shampooing a deep chestnut coloration having a slight violet tinge.

EXAMPLE 23

The following dyeing composition is prepared:

| | |
|---|---|
| Dihydrochloride of 4-β-ethoxyethylamino aniline | 0.85 g |
| Dihydrochloride of (2,4-diamino) phenoxyethanol | 0.05 g |
| Lauric alcohol at 10.5 mole of ethylene oxide | 4.5 g |
| Ammonia at 22° B. | 10 g |
| Water, q.s. | 100 g |

The pH is 10.7. At the moment of use one adds 80 g of hydrogen peroxide at 20 volumes. This mixture applied for 25 minutes at 20° to bleached hair imparts thereto, after rinsing and shampooing, a blue grey color having metallic glints.

EXAMPLE 24

The following dyeing composition is prepared:

| | |
|---|---|
| Dihydrochloride of 4-amino-N-γ-methoxypropyl aniline | 0.3 g |
| Paraaminophenol | 0.12 g |
| 2-methyl-5-amino-N-β-hydroxyethyl phenol | 0.095 g |
| 2,6-dimethyl-5-acetylamino phenol | 0.1 g |
| Oleic alcohol oxyethylenated at 2 moles of ethylene oxide | 4.5 g |
| Oleic alcohol oxyethylenated at 4 moles of ethylene oxide | 9 g |
| Propyleneglycol | 9 g |
| Ammonia at 22° B. | 10 g |
| Water, q.s. | 100 g |

The pH is 10.5. At the moment of use, one adds 85 g of hydrogen peroxide at 20 volumes.

This mixture applied to bleached hair for 30 minutes at 25° C. imparts thereto, after rinsing and shampooing, a burnt blonde coloration.

It is well understood that the method of preparation and the examples of compositions given above are in no way limiting and may give way to all desirable modifications without thereby departing from the scope of the invention.

What is claimed is:

1. A dyeing composition for keratinic fibers comprising an aqueous solution containing a dyeing amount of at least one dye compound having the formula:

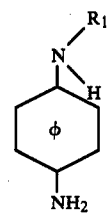

in which $R_1$ is $-(CH_2)_n-OR$, R is methyl or ethyl, n is 2 or 3, or one of the corresponding acid salts.

2. The composition of claim 1 which also contains a solvent for increasing the solubility of said dye compound.

3. The composition of claim 2 in which said solvent for increasing the solubility of said dye compound is selected from the group consisting of ethanol, isopropanol, glycerine, butylglycol, ethylene-glycol, propylene-glycol, monoethylether of diethylene-glycol and monomethylether of diethylene-glycol.

4. The composition of claim 1 which contains from 0.001% to 6% by weight of the dye compounds in proportion to the total weight of the composition.

5. The composition of claim 1 in which the pH is between 8 and 11.5.

6. The composition of claim 5 which also contains an alkalizing agent selected from the group consisting of ammonia, alkyl amines, alkanolamines, and sodium and potassium hydroxides and carbonates.

7. The composition of claim 1 which also contains at least one oxidation dye selected from the group consisting of paraphenylenediamines and paraaminophenols.

8. The composition of claim 1 which also contains at least one coupler for said dye compound.

9. The composition of claim 8 in which the coupler is selected from the group consisting of meta-phenylenediamines, metaaminophenols, 6-hydroxy benzomorpholine and 2,6-dimethyl-3-acetylamino phenol.

10. The composition of claim 1 which also contains at least one direct nitrated dye of the benzene series.

11. The composition of claim 1 which also contains at least one dye selected from the group consisting of a leuco-derivative of indoanilines and indophenols.

12. The composition of claim 1 which also contains at least one product selected from the group consisting of polyaminophenols, monoaminodiphenols, diaminodiphenols and polyphenols.

13. The composition of claim 1 which also contains at least one hydro-soluble surface active agent in a proportion between 0.5 and 30% by weight in proportion to the total weight of the composition.

14. The composition of claim 1 which also contains at least one organic solvent in a proportion comprised between 1 and 40% by weight in proportion to the total weight of the composition.

15. The composition of claim 1 which also contains at least one thickening product in a proportion between 0.5 and 5% by weight in proportion to the total weight of the composition.

16. The composition of claim 1 which also contains at least one anti-oxidizing agent in a proportion between 0.5 and 1% by weight in proportion to the total weight of the composition.

17. The composition of claim 1 which also contains at least one penetrating agent or one sequestrating agent.

18. The process of dyeing keratin materials comprising contacting said keratinic material with an oxidizing agent and a dyeing amount of the composition of claim 1.

19. The process of claim 18 in which said keratinic material is human hair.

* * * * *